(12) United States Patent
Jung

(10) Patent No.: US 11,185,686 B2
(45) Date of Patent: Nov. 30, 2021

(54) INTENSIVE CARE DEVICE USING ANIONS

(71) Applicant: FR MEDICAL LAB CO., LTD., Daegu (KR)

(72) Inventor: Ki-Sub Jung, Seoul (KR)

(73) Assignee: FR MEDICAL LAB CO., LTD., Daegu (KR)

( * ) Notice: Subject to any disclaimer, the term of this patent is extended or adjusted under 35 U.S.C. 154(b) by 0 days.

(21) Appl. No.: 16/474,954

(22) PCT Filed: Jan. 25, 2017

(86) PCT No.: PCT/KR2017/000848
§ 371 (c)(1),
(2) Date: Jun. 28, 2019

(87) PCT Pub. No.: WO2018/124367
PCT Pub. Date: Jul. 5, 2018

(65) Prior Publication Data
US 2019/0336755 A1    Nov. 7, 2019

(30) Foreign Application Priority Data

Dec. 30, 2016    (KR) .................... 10-2016-0183804

(51) Int. Cl.
*A61N 1/14* (2006.01)
*A61N 1/04* (2006.01)
*A61N 1/02* (2006.01)
(Continued)

(52) U.S. Cl.
CPC ............... *A61N 1/14* (2013.01); *A61N 1/025* (2013.01); *A61N 1/0472* (2013.01);
(Continued)

(58) Field of Classification Search
CPC ........ A61N 1/14; A61N 1/025; A61N 1/0472; A61N 1/0504; A61N 5/0601;
(Continued)

(56) References Cited

FOREIGN PATENT DOCUMENTS

| KR | 10-2005-0006944 A | 1/2005 |
|---|---|---|
| KR | 1020050006944 | 1/2005 |

(Continued)

OTHER PUBLICATIONS

KR Office Action dated Aug. 27, 2018 as received in Application No. 10-2016-0183804.
(Continued)

*Primary Examiner* — Mark Bockelman
(74) *Attorney, Agent, or Firm* — Maschoff Brennan

(57) ABSTRACT

The present invention relates to an intensive care device using anions, the device: intensively irradiating the affected area with anions such that the affected area is quickly healed, and allowing a patient's body to be in an electrostatically induced condition through grounding, and, in this condition, irradiating the affected area with anions such that an anionic charge is induced in the patient's body direction with linearity, thereby having excellent effects by minimizing anionic loss caused by cations in the air and maximizing the amount of irradiation directed toward the affected area; having a low-output light irradiation lens irradiated with blue wavelength light, which is a low-output ray, so as to exhibit a physically beneficial effect such as skin sterilization; and having a simple use and procedure compared with skin grafting or other medicines and medical supplies for skin regeneration.

6 Claims, 7 Drawing Sheets

(51) Int. Cl.
*A61N 1/05* (2006.01)
*A61N 5/06* (2006.01)

(52) U.S. Cl.
CPC ......... *A61N 1/0504* (2013.01); *A61N 5/0601* (2013.01); *A61N 5/0616* (2013.01); *A61N 5/0624* (2013.01); *A61N 2005/0612* (2013.01); *A61N 2005/0652* (2013.01); *A61N 2005/0659* (2013.01); *A61N 2005/0663* (2013.01)

(58) Field of Classification Search
CPC ................ A61N 5/0616; A61N 5/0624; A61N 2005/0612; A61N 2005/0652; A61N 2005/0659; A61N 2005/0663; A61N 5/06; A61N 2005/0642
See application file for complete search history.

(56) References Cited

FOREIGN PATENT DOCUMENTS

| | | |
|---|---|---|
| KR | 10-0793861 B1 | 1/2008 |
| KR | 10-0798902 B1 | 1/2008 |
| KR | 10-2010-0101420 A | 9/2010 |
| KR | 10-2012-0054704 A | 5/2012 |
| KR | 1020120054704 | 5/2012 |
| KR | 10-2014-0002835 A | 1/2014 |
| KR | 10-1419720 B1 | 8/2014 |
| KR | 10-1552531 B1 | 9/2015 |

OTHER PUBLICATIONS

KR Decision of Grant dated Sep. 28, 2018 as received in Application No. 10-2016-0183804.

INTENSIVE CARE DEVICE USING ANIONS

TECHNICAL FIELD

The present invention relates to an intensive care device using anions, and more particularly to an intensive care device which promptly heals the injured portion by intensively irradiating anions to the injured portion, wherein the human body of the patient is brought into an electrostatically induced condition due to grounding, and in this state, if anions are irradiated to the injured portion, the anionic charges have straightness and are guided toward the human body of the patient so that the loss of the anions by the cations in the air is minimized and the dosage of the anions toward the injured portion is maximized, showing an excellent effect, in which a low-output light irradiation lens which irradiates light of a blue wavelength that is a low-output light ray is provided to show a useful effect, such as sterilization of skin, to the human body, and in which the use and surgical procedure of the intensive care device is simpler than a skin implant therapy or other skin regeneration medicines.

BACKGROUND ART

Generally, it is known in the medical world that it is helpful to care of an injury to send a predetermined amount of currents or ultrasonic waves to the injury, and related equipment has already been supplied. However, the effects of the care method using electricity may be different according to the state, the size, and the degree of an injury, and cannot be widely used publicly due to the difficulty of use because the method is a contact type method in which the care device has to directly contract the injury. Similarly, the use of a care method using ultrasonic waves is also restrictive for the same reason as the electrical care.

In this way, when an in-use problem for the care method in which the device has to directly contact the injury during an electrical care or an ultrasonic care is solved, the method can be greatly helpful to many patients, and as one of the methods, a method for irradiating anions to the skin tissues in a non-contact manner by using ionization of a current may be used.

Meanwhile, a skin cosmetic device which supplies anions as well as steam to skin, for example, of a face by using an anion generating device has been developed, and as known, the anions remove waste products and keratin when the anions contact the skin surface. Moreover, it is known to be effect to activation of cells as well as anti-aging.

In general, an anion generating device is embedded for discharging anions, and the anions generated by the anion generating device has no specific directionality and the movement path of the anions are not long. Accordingly, only some of the anions generated by the anion generating device can be delivered to the surface of skin, for example, of the face of a user and be absorbed. In addition, since the anions generated by the anion generating device has characteristics in which the anions are neutralized by a large number of cations distributed in the air in the movement path to the skin of the user, the effects significantly deteriorate before the anions reach the surface of the skin of the user.

DETAILED DESCRIPTION OF THE INVENTION

Technical Problem

Accordingly, the present invention provides an intensive care device using anions which promptly heals the injured portion by intensively irradiating anions to the injured portion, wherein the human body of the patient is brought into an electrostatically induced condition due to grounding, and in this state, if anions are irradiated to the injured portion, the anionic charges have straightness and are guided toward the human body of the patient so that the loss of the anions by the cations in the air is minimized and the dosage of the anions toward the injured portion is maximized, showing an excellent effect.

Technical Solution

The above-mentioned objects of the present invention are achieve by an intensive care device using anions comprising: a body part in which a main board is mounted in the interior thereof, in which a touchscreen is provided on a front surface thereof, and in which moving wheels are installed on the lower side thereof; a head part connected to one side of the body part by an arm hinge to be movable, and in which an anion generating unit electrically connected to the main board is operatively installed; an anion irradiating part connected to one side of the head part such that the angle thereof is adjusted and electrically connected to the anion generating unit such that anions generated from the anion generating unit is irradiated to an outside through an end thereof; and a human body grounding device electrically connected to the anion generating unit, and electrically grounded to a portion of the human body of a patient such that the in-air loss of the anions irradiated from the anion irradiating part by an electrostatic induction phenomenon due to grounding of the human body is minimized and the dosage of the anions to the human body of the patient is maximized.

According to the present invention, the anion generating unit may include: a terminal panel; and a plurality of anon modules mounted on the terminal panel and configured to generate anions, and the anon modules may be connected to the main board to supply electric power to the main board, may be connected to the anion irradiating part to supply anions to the anon irradiating part, and may be connected to the human body grounding device such that the human body grounding device is grounded to the human body.

According to the present invention, each of the anion module may include: an oscillation part oscillated and amplified by using a power source voltage to generate an input voltage and providing the generated input voltage to a transformer; a transformer configured to boost and output the input voltage; a grounding part electrically connecting one end of an output side of the transformer, and an electrode contacting the human body; and a high-voltage generating part electrically connected to opposite ends of an output side of the transformer, and configured to convert the boosted voltage of the transformer to a high voltage and provide the high voltage to anion irradiating needles through an output side.

According to the present invention, the grounding part may include: a rectification element, of which one terminal is connected to one end of the output side; and a grounding terminal connected to an opposite terminal of the rectification element and the electrode.

According to the present invention, the high voltage generating part 2124 may include: a voltage doubling/rectifying circuit configured to double and rectify voltages of opposite ends of the output side of the transformer.

According to the present invention, the anion irradiating part may include a pair of connecting members connected to the head part in a bellows tube manner such that the angles thereof is adjusted; and irradiation members installed at ends of the pair of connecting members, respectively, and configured to irradiate anions.

According to the present invention, the light irradiation member may include: anion irradiating needles protruding from a lower surface of the corresponding one of the pair of irradiation members, the number of which corresponds to the number of the anion generating units, electrically connected to the anion generating unit, and a tip end of which is manufactured in a sharp needle shape such that anions are irradiated through the end thereof; a low-output light irradiation lens provided on a lower surface of the corresponding one of the pair of irradiation members to be turned on and off and from which light of a blue wavelength is irradiated; and a sensor protruding from the lower surface of the corresponding one of the pair of irradiation members, and extending further than the anion irradiating needle such that an operation of the intensive care device using anions is interrupted when an end of the sensor connected to a portion of the human body.

According to the present invention, among the plurality of anon modules, the half of the anion modules may be electrically connected to one of the anion irradiating needles and the remaining half of the anion modules may be electrically connected to the other of the anion irradiating needles, and the anion modules electrically connected to the one of the anion irradiating needles and the anion modules electrically connected to the other of the anion irradiating needles may be independently electrically connected to the human body grounding device.

Advantageous Effects of the Invention

The above-described intensive care device using anions promptly heals the injured portion by intensively irradiating anions to the injured portion and the human body of the patient is brought into an electrostatically induced condition due to grounding, and in this state, if anions are irradiated to the injured portion, the anionic charges have straightness and are guided toward the human body of the patient so that the loss of the anions by the cations in the air is minimized and the dosage of the anions toward the injured portion is maximized, showing an excellent effect.

Further, second, a low-output light irradiation lens which can selectively irradiate light of a blue wavelength, a red wavelength, and an infrared wavelength is provided to show a useful effect, such as regeneration of skin and improvement of wrinkles, to the human body.

Further, third, the use and surgical procedure of the intensive care device is simpler than a skin implant therapy or other skin regeneration medicines.

BEST MODE

Hereinafter, preferred embodiments of the present invention will be described in detail with reference to the accompanying drawings. However, the preferred embodiments of the present invention are provided to describe the present invention so that an ordinary person in the art to which the present invention pertains can easily carry out the present invention, and accordingly, the technical spirit and scope of the present invention are not limited by the embodiments.

Figure 1:
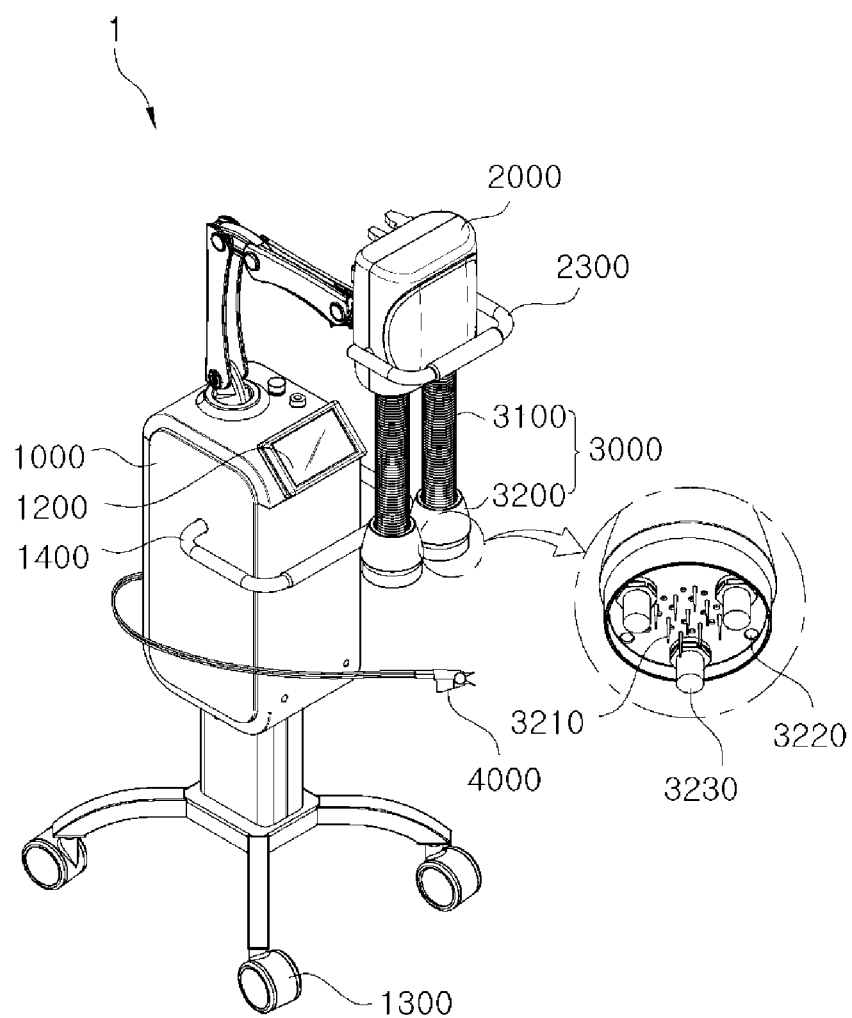
FIG. 1 is a perspective view of an intensive care device using anions according to an embodiment of the present invention.
Figure 2:
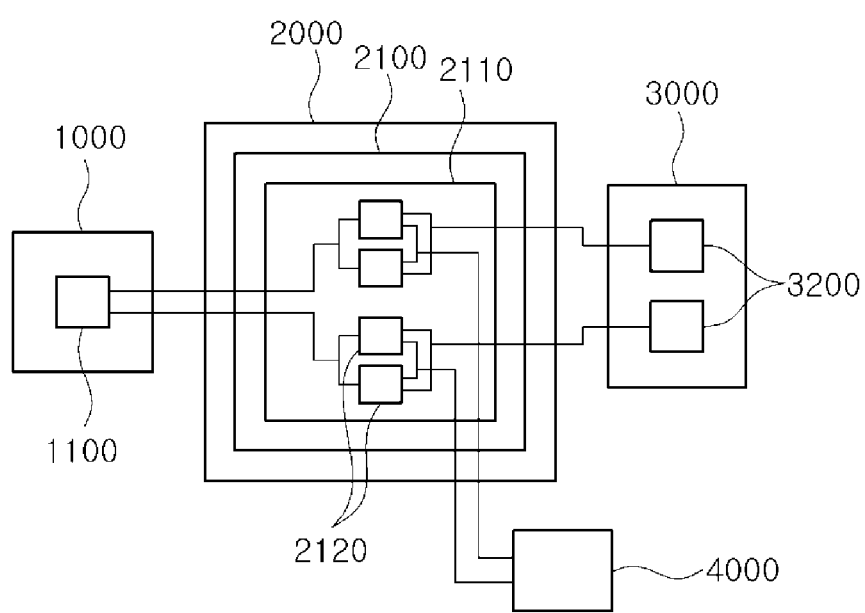
FIG. 2 is a block diagram of the intensive care device using anions according to the embodiment of the present invention.
Figure 3:
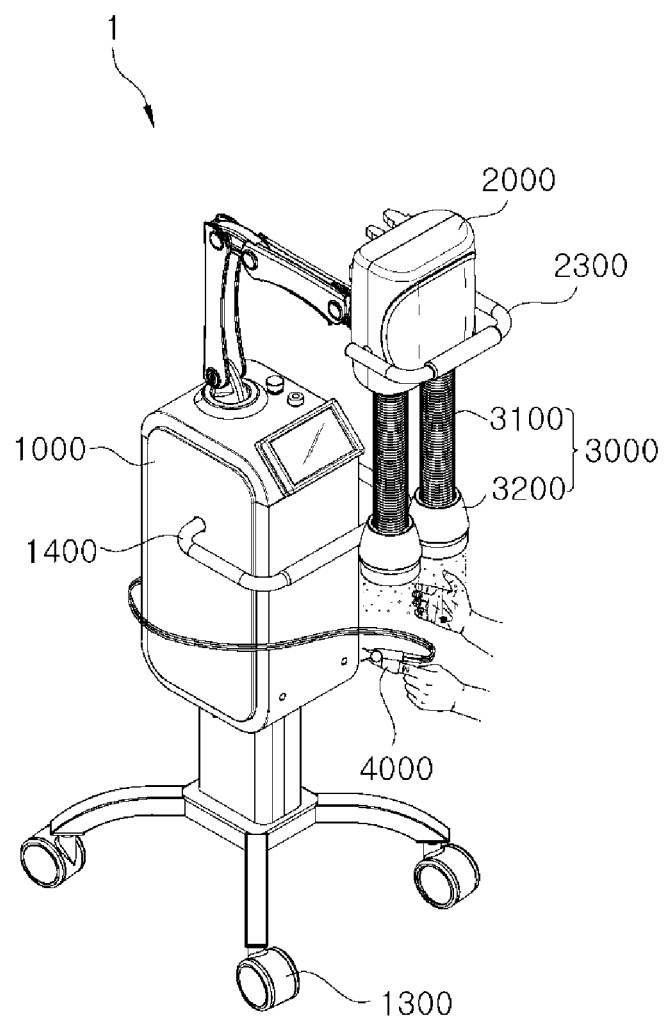
FIG. 3 is a view illustrating an in-use state of the intensive care device using anions according to the embodiment of the present invention.
Figure 4:
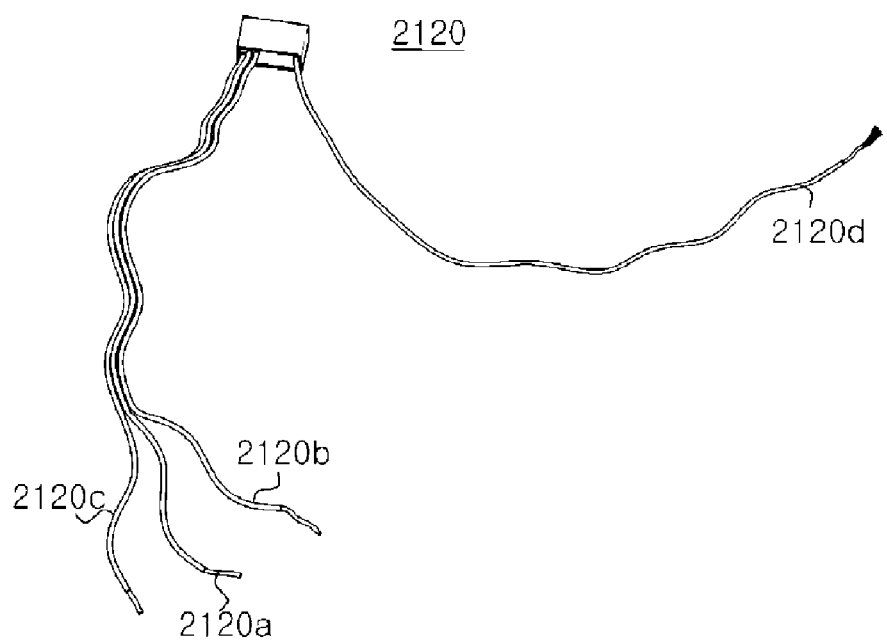
FIG. 4 is a circuit diagram of a unit anion module according to an embodiment of the present invention.
Figure 5:
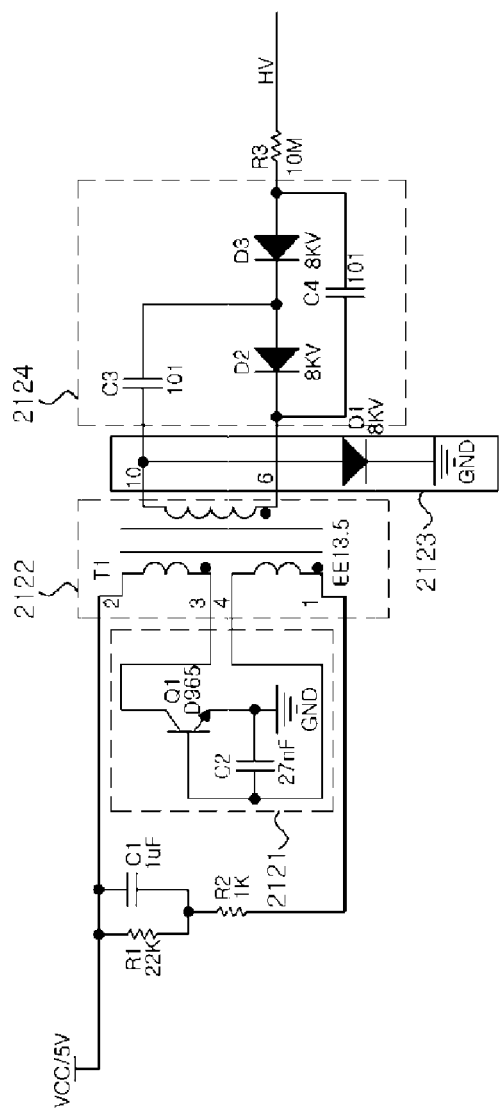
FIG. 5 is a perspective view of the unit anion module according to the embodiment of the present invention.
Figure 6:
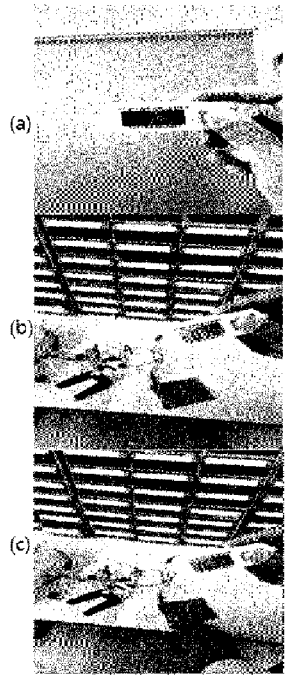
FIG. 6 is a photo showing an anion concentration experiment according to whether the intensive care device using anions according to the embodiment of the present invention is grounded.

FIG. 1 is a perspective view of an intensive care device using anions according to an embodiment of the present invention. FIG. 2 is a block diagram of the intensive care device using anions according to the embodiment of the present invention. FIG. 3 is a view illustrating an in-use state of the intensive care device using anions according to the embodiment of the present invention. FIG. 4 is a photo showing an anion concentration experiment according to whether the intensive care device using anions according to the embodiment of the present invention is grounded. FIGS. 5 and 6 are graphs depicting an experiment of the intensive care device using anions according to the embodiment of the present invention.

An intensive care device using anions according to a preferred embodiment of the present invention includes a body part in which a main board is mounted in the interior thereof, in which a touchscreen is provided on a front surface thereof, and in which moving wheels are installed on the lower side thereof, a head part connected to one side of the body part by an arm hinge to be movable, and in which an anion generating unit electrically connected to the main board is operatively installed, an anion irradiating part connected to one side of the head part such that the angle thereof is adjusted and electrically connected to the anion generating unit such that anions generated from the anion generating unit is irradiated to the outside through an end thereof, and a human body grounding device electrically connected to the anion generating unit, and electrically grounded to a portion of the human body of a patient such that the in-air loss of the anions irradiated from the anion irradiating part by an electrostatic induction phenomenon due to grounding of the human body is minimized and the dosage of the anions to the human body of the patient is maximized.

Hereinafter, the elements of the intensive care device 1 using anions and operational relationships between the elements according to the preferred embodiment of the present invention will be described in detail with reference to FIGS. 1 to 3.

The elements, which will be described below, are operatively installed in the above-described body part 1000, electric power that is necessary for an operation of the intensive care device 1 is supplied to the body part 1000, and an overall control of the system is made by the body part 1000, wherein the main board 1100 is mounted in the interior of the body part 1000, the touchscreen 12000 is provided on the front surface of the body part 1000, and the moving wheels 13000 are installed on the lower side of the body part 1000.

The main board 1100 is electrically connected to the head part 2000, the anion irradiating part 3000, and the human body grounding device 4000, which will be described below, and the above-described touchscreen 12000 also is electrically connected to the main board 1100 such that a control, for example, an on/off control of the entire system through a touch manner is made. Further, the moving wheels 13000 are provided with separate handles 14000 which makes it easy to move and transport the intensive care device 1 using anions and may be gripped.

The head part 2000 is provided on the upper side of the above-described body, and the head part 2000 generates anions and is connected to the body by the arm hinge 2200 to be movable, and the anion generating unit 2100 electrically connected to the main board 1100 is operatively installed in the head part 2000. Further, the head part 2000 is provided with a separate handle 23000 like the body part 1000.

The above-described anion generating unit 2100 includes a terminal panel 2100, and a plurality of anon modules 2120 mounted on the terminal panel 2110 and configured to generate anions, and the anon modules 2120 are connected to the main board 1100 to supply electric power to the main board 1100, are connected to the anion irradiating part 3000, which will be described below, to supply anions to the anon irradiating part 3000, and are connected to the human body grounding device 4000 such that the human body grounding device 4000 is grounded to the human body.

Among the plurality of anon modules 2120 mounted on the above-described terminal panel 2110, the half of the anion modules 2120 are connected to anion irradiating needles 3210 of one anion irradiating part 3000 in one-to-one correspondence, and the remaining half of the anion modules 2120 are connected to anion irradiating needles 3210 of the other anion irradiating part 3000 in one-to-one correspondence. Further, the anion modules 2120 divided into two parts and independently connected to the anion irradiating parts 3000 also are independently connected to the human body grounding device 4000, which will be described below. That is, the anion modules 2120 connected to the one anion irradiating part 3000 are integrated into one and are connected to the human body grounding device 4000, and the anion modules 2120 connected to the other anion irradiating part 3000 are integrated into another one and are connected to the human body grounding device 4000.

Further, the anion irradiating parts 3000 are connected to the lower side of the above-described head part 2000 such that the angles thereof may be adjusted, and are located close to the human body of the patient who requires a care, and are electrically connected to the anion generating unit 2100 such that the anions generated from the anion generating unit 2100 is irradiated to the outside through ends of the anion irradiating parts 3000.

Each of the anion irradiating parts 3000 includes a pair of connecting members 3100 connected to the head part 2000 in a bellows tube manner such that the angles thereof may be adjusted, and irradiation members 3200 installed at ends of the pair of connecting members 3100, respectively, and configured to irradiate anions.

The angles of the above-described connecting members 3100 may be adjusted flexibly, and the locations of the connecting members 3100 may be fixed in a state in which the angles thereof are adjusted, and accordingly, the light irradiation members 3200 may be controlled to face an injury even when the injury is generated in any portion of the human body.

Further, each of the light irradiation members 3200 includes an anion irradiating needle 3210 protruding from a lower surface of the corresponding one of the pair of irradiation members 3200, the number of which corresponds to the number of the anion generating units 2100, electrically connected to the anion generating unit 2100, and a tip end of which is manufactured in a sharp needle shape such that anions are irradiated through the end thereof, a low-output light irradiation lens 3220 provided on a lower surface of the corresponding one of the pair of irradiation members 3200 to be turned on and off and from which light of a blue wavelength is irradiated, and a sensor 3230 protruding from the lower surface of the corresponding one of the pair of irradiation members 3200, and extending further than the anion irradiating needle 3210 such that an operation of the intensive care device 1 using anions is interrupted when an end of the sensor 3230 connected to a portion of the human body.

The above-described anion irradiating needles 3210 are connected to the anion modules 2120 in one-to-one correspondence to directly irradiate anions generated from the anion modules 2120, and the tip ends of the anon irradiating needles 3210 has a sharp linear needle shape such that anions may be irradiated while having straightness. The anion irradiating needles 3210 may be installed to correspond to the change of the numbers of the anion modules 2120. That is, if the number of the anion modules 2120 increases, the number of the anion irradiating needles 3210 also increases in correspondence to the number of the anion modules 2120, and if the number of the anion modules 2120 decreases, the number of the anion irradiating needles 3210 also decreases in correspondence to the number of the anion modules 2120, Further, the light irradiated from the low-output light irradiation lens 3220 is light of a blue wavelength, and is irradiated in a state in which after electric energy passes through a light emitting diode (LED), the electric energy is converted into a low-output ray having a wavelength of 430 nm to 460 nm, and is used for the purpose of sterilization.

Further, the above-described sensor 3230 contacts skin prior to the anion irradiating needles 3210 when the light irradiation member 3200 becomes close to the skin more than necessary to prevent the patient from being exposed to a current of high voltage formed in the anion irradiating needles 3210. It is preferable that the sensor 3230 is a proximity sensor or a contact sensor according to the related art.

Meanwhile, the human body grounding device 4000 is electrically connected to the above-described anion generating unit 2100, and the human body grounding device 4000 is electrically grounded to a portion of the human body of the patient, wherein the in-air loss of the anions irradiated from the anion irradiating parts 300 is minimized and the dosage of the anions to a portion of the human body of the patient is maximized by an electrostatic induction phenomenon due to grounding of the human body. As illustrated in the drawings, the human body grounding device 4000 may be grounded to a finger of the patient but may be grounded to various portions of the human body, and the shape of the human body grounding device 4000 may be formed in a shape which may be ground to various portions of the human body.

Anions move toward the skin of the patient at a high speed if the electrostatic induction operation is generated in the human body of the patient by the human body grounding device 4000 and the anions neutralized by the cations in the air while moving may be minimized, and the anions may be intensively irradiated to a portion which is close to the light irradiation member 3200 regardless of the portion of the human body. This is the same as the principle of absorbing a thunderbolt by a lightning rod, and the anions are rapidly irradiated to the grounded portion of the human body.

Hereinafter, the anion module according to the present invention will be described in detail with reference to FIGS. 4 and 5. First, FIG. 4 is a circuit diagram of a unit anion module according to an embodiment of the present invention. FIG. 5 is a perspective view of the unit anion module according to the embodiment of the present invention.

As can be seen in FIG. 6, an oscillation part 2121 includes, for example, a modified circuit of a Colpitts oscillator or a Hartley oscillator. The oscillation part 2121 is connected to the main board 1100 and includes a TR (Q1) which performs an oscillation and amplification operation, and a a capacitor (C2) connected between a base and an emitter of the TR (Q1), and an emitter terminal of the TR (Q1) is grounded. Further, a collector terminal of the TR (Q1) is connected to a first terminal (e.g., No. 3 pin) of a transformer 2122, and a base terminal of the TR (Q1) is connected to a second terminal (e.g., No. 4 pin) of the transformer 2122. Power source voltage terminals of the oscillation part 2121 are terminals connected to a first electric wire 2120*a* and a second electric wire 2120*b* of the anion module 2120 in FIG. 4, respectively, and the anion module 2120 receives a voltage of DC 5V from a power source part (not illustrated) connected to the main board 1100 though the first electric wire 2120*a* and the second electric wire 2120*b* of FIG. 4. Since the TR (Q1) may be freely replaced with a FET and the like, the embodiment of the present invention is not specifically limited to the TR (Q1).

The transformer 2122 includes a voltage conversion part, for example, a booster. The oscillation part 2121 is electrically connected to an input-side terminal, that is, a primary coil of the transformer 2122, and a grounding part 2123 and a high-voltage generating part 2124 are electrically connected to an output-side terminal, that is, a secondary coil of the transformer 2122.

The grounding part 2123 includes a rectifying element, for example, a diode connected to one terminal of an output side of the transformer 2122, and a grounding terminal connected to a cathode terminal of the diode. Here, the grounding terminal is electrically connected to a portion of the human body by the grounding wire. As illustrated in FIGS. 1 and 2, the grounding terminal is leaded by a third electric wire 2120*c* and is connected to the human body through the human body grounding device 4000. Although a diode has been exemplified for convenience of description, for example, a TR or an FET may be freely used like the diode, and the embodiment of the present invention is not specifically limited to the diode. For example, the TR may be used like the diode by connecting the base and the collector.

The high-voltage generating part 2124 includes a voltage doubled rectification circuit according to the embodiment of the present invention. The high-voltage generating part 2124 includes diodes D2 and D3 connected in series to an opposite terminal of an output side of the transformer 2122 in an inverse direction, and a resistor R3 connected to the anode of the diode D3, and includes capacitors C3 connected to the two diodes D2 and D3 connected in series and one terminal of an output side of the transformer 2122. In this way, the high-voltage generating part 2124 is electrically connected to opposite ends (terminals) of an output side of the transformer 2122. The resistance R3 is connected to the anion irradiating needles 3210 which receive a high voltage and generate anions. A fourth electric wire 2120*d* is leaded from an output side (HV) of the high-voltage generating part 2124 and is connected to the anion irradiating needles 3210. It is preferable that the high-voltage generating part 2124 generates a high voltage of a range in which ozone is not generated in the anion irradiating needles 3210.

According to the configuration, if a voltage of DC 5V is applied, an instantaneous current flows to the TR (Q1) (e.g., Nos. 2 and 3 coils of T1), and a voltage induced to No. 4 and No. 1 of the transformer 2122 is generated by the current. If an opposite polarity is input such that the organic voltage is connected to the base of the TR (q1) and is amplified, an operation by a pulse once generated is continuously generated so that the operation continues permanently as long as the electric power is supplied. With the oscillation operation generated in this way, a voltage (e.g., several hundred times or several thousand times, less than 4000 V according to the number of windings of the coil) included to No. 10 and No. 6 of the transformer 2122 is generated. The high voltage (e.g., an AC pulse form) generated in this way is doubled (e.g., doubled voltage, about 5000 V to 6500 V) and rectified (e.g., 2500 V to 3000 V) through the diodes D2 and D3 and is leaded by the fourth electric wire 2120*d* on the output side HV of the high-voltage generating part 2124 such that anions may be discharged through the anion irradiating needles 3210.

In other words, if a positive (+) voltage is applied to No. 10 terminal of the transformer 2122, positive charges flow to the ground, and if a negative (−) voltage is applied, the negative voltage is applied from the output side HV of the high-voltage generating part 2124 to the anion irradiating needles 3210. Due to the applied voltage, anions are discharged through the anion irradiating needles 3210. In this process, since the anions generated by the high voltage of the high-voltage generating part 2124 have straightness due to the electrostatic induction operation as the grounding part 2123 is ground to the human body (e.g., a finger) through the human body grounding device 4000, the cations are not neutralized in the air and are intensively irradiated to the human body.

Hereinafter, a preferred example according to use of intensive care device 1 using anions and operational relationships between the elements according to the preferred embodiment of the present invention will be described in detail with reference to FIGS. 6 to 8.

TABLE 1

| Category | Whether voltage of intensive care device using anions is applied | Whether human body of patient is grounded | Amount of ions generated (ion/cc) |
| --- | --- | --- | --- |
| Photo (a) | Not applied | Not grounded | 70,000 |
| Photo (b) | Not applied | Not grounded | 700,000 |
| Photo (c) | Applied | Grounded | 16,310,000 |

Referring to Table 1 and FIG. 6, the amount of ions in the air measured when (photo a) the electric power of the intensive care device 1 using anions according to the present invention was not applied and the human body of the patient was not grounded was 70,000 ion/cc.

Further, the amount of ions irradiated from the light irradiation member 3200 toward the skin of the patient when (photo b) the electric power of the intensive care device 1 using anions according to the present invention was applied but the human body of the patient was not grounded was 700,000 ion/cc.

Further, the amount of ions irradiated from the light irradiation member 3200 toward the skin of the patient when (photo c) the electric power of the intensive care device 1 using anions according to the present invention was applied and the human body of the patient was grounded was 16,310,000 ion/cc.

It can be seen that the amount of anions irradiated from the light irradiation member 3200 toward the skin of the patient was increased by 23.3 times by the grounding of the human body through the human body grounding device 4000.

Next, referring to FIGS. 7 and 8, this experiment was a comparative experiment for an injury care effect using an anion care device (an intensive care device 1 using anions according to the present invention, hereinafter the same) and a Medifoam (manufacturer: Genewell/Marketer: Il-dong Pharmacy) which is a known band type treatment agent attached to an injury after an arbitrary wounding is induced in a skin tissue of pig.

First, in a state in which the anion care device was made to maximally approach the injury, anions were irradiated for 30 minutes on the 0-th, 4-th, 7-th, 10-th, 14-th, 17-th, 21-th, 25-th, 28-th, 31-th, and 35-th days, and then the experiment was performed in a state in which the pig, which is an experimental target, was grounded for electrostatic induction.

Further, as in the Medifoam, new ones were exchanged on the 0-th, 4-th, 7-th, 10-th, 14-th, 17-th, 21-th, 25-th, 28-th, 31-th, and 35-th days, and were attached to the injury.

Figure 7:
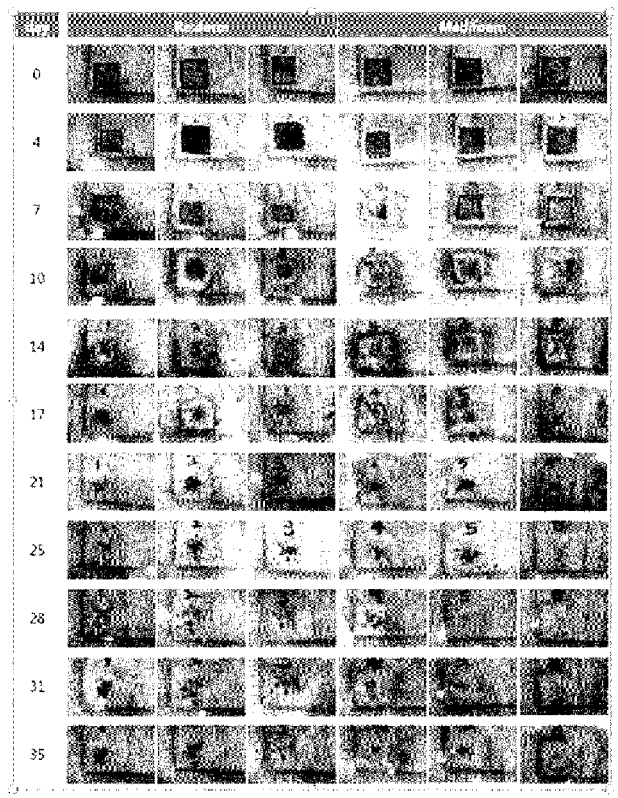
FIGS. 7 and 8 are graphs depicting an experiment of the intensive care device using anions according to the embodiment of the present invention.

FIG. 7 is an image obtained by photographing the injury cared by using the anion care device on the 0-th, 4-th, 7-th, 10-th, 14-th, 17-th, 21-th, 25-th, 28-th, 31-th, and 35-th days, the injury for the dates by using Medifoam.

Figure 8:
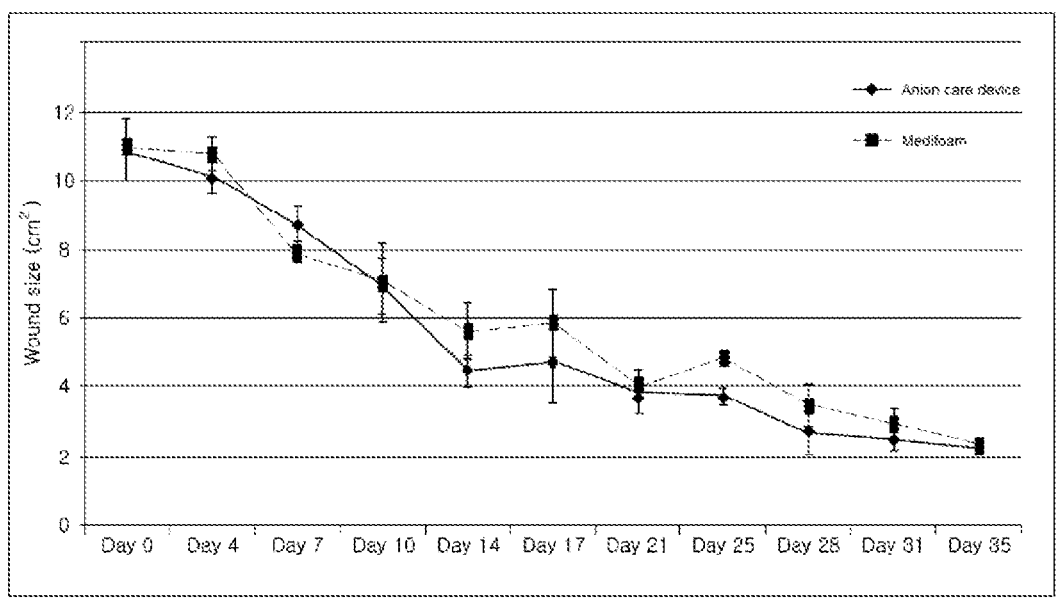

FIG. 8 is a graph depicting change values for the areas of the injury cared by using the anion care device on the 0-th, 4-th, 7-th, 10-th, 14-th, 17-th, 21-th, 25-th, 28-th, 31-th, and 35-th days, the injury for the dates by using Medifoam.

patient is brought into an electrostatically induced condition due to grounding, and in this state, if anions are irradiated to the injured portion, the anionic charges have straightness and are guided toward the human body of the patient so that the loss of the anions by the cations in the air is minimized and the dosage of the anions toward the injured portion is maximized, showing an excellent effect.

Further, a low-output light irradiation lens 3220 which irradiates light of a blue wavelength that is a low-output light ray is provided to show a useful effect, such as sterilization of skin, to the human body. Further, the use and surgical procedure of the intensive care device is simpler than a skin implant therapy or other skin regeneration medicines.

In spite that several embodiments have been exemplified, it is apparent to an ordinary person in the art to which the present invention pertains that the present invention can be specified in various forms without departing from the purpose and the scope of the present invention. Accordingly, the above-mentioned embodiments should be construed not to be restrictive but to be exemplary, and all the embodiments within the claims and the equivalents thereof will fall within the scope of the present invention.

DESCRIPTION OF REFERENCE NUMERALS

| | |
|---|---|
| 1: intensive care device using anions | |
| 1000: body part | 1100: main board |
| 1200: touchscreen | 1300: moving wheel |
| 1400: handle | 2000: head part |
| 2100: anion generating unit | 2110: terminal panel |
| 2120: anion module | |
| 2121: oscillation part | 2122: transformer |
| 2123: grounding part | 2124: high-voltage generating part |
| 2200: arm hinge | 2300: handle |
| 3000: anion irradiating part | 3100: connecting member |
| 3200: irradiation member | 3210: anion irradiating needle |
| 3220: irradiation lens | 3230: sensor |
| 4000: body grounding device | |

TABLE 2

| group | no. | Day 0 | Day 4 | Day 7 | Day 10 | Day 14 | Day 17 | Day 21 | Day 25 | Day 28 | Day 31 | Day 35 |
|---|---|---|---|---|---|---|---|---|---|---|---|---|
| Re: derm | 1 | 113.78 | 106.67 | 90.22 | 69.44 | 51.33 | 51.33 | 38.00 | 40.00 | 21.67 | 25.00 | 24.56 |
| | 2 | 132.22 | 117.33 | 103.33 | 87.11 | 53.78 | 66.67 | 51.33 | 44.33 | 34.00 | 32.11 | 28.44 |
| | 3 | 116.67 | 113.78 | 96.44 | 75.11 | 44.44 | 40.00 | 39.67 | 40.00 | 34.00 | 26.67 | 22.67 |
| | sd | 9.92 | 5.43 | 6.56 | 9.02 | 4.84 | 13.38 | 7.26 | 2.50 | 7.12 | 3.72 | 2.95 |
| | mean | 120.89 | 112.59 | 96.67 | 77.22 | 49.85 | 52.67 | 43.00 | 41.44 | 29.89 | 27.93 | 25.22 |
| Medifoam | 4 | 124.67 | 113.67 | 90.00 | 63.89 | 61.33 | 58.78 | 44.44 | 53.67 | 35.89 | 32.00 | 24.56 |
| | 5 | 120.89 | 121.00 | 90.22 | 87.00 | 72.22 | 78.00 | 44.00 | 53.78 | 46.44 | 38.00 | 28.44 |
| | 6 | 120.56 | 124.44 | 84.00 | 83.78 | 53.78 | 58.67 | 46.67 | 53.78 | 34.00 | 28.44 | 24.89 |
| | sd | 2.28 | 5.50 | 3.53 | 12.52 | 9.27 | 11.13 | 1.43 | 0.06 | 6.71 | 4.83 | 2.16 |
| | mean | 122.04 | 119.70 | 88.07 | 78.22 | 62.44 | 65.15 | 45.04 | 53.74 | 38.78 | 32.81 | 25.96 |

Further, Table 2 was obtained by calculating ratios of the areas for the dates for the injury, and was calculated in area ratio=measured area for periods/entire area (3*3 cm)*1000.

Accordingly, referring to Table 2 and the graphs, the care method using an anion care device showed a care effect that is similar to that of the care method using Medifoam, and it appeared that the care method using Medifoam was rather effective until the 4-th day, but it is identified that the care method using an anion care device was more effective than the care method using Medifoam from the 7-th to 35-th days.

The above-described intensive care device 1 using anions promptly heals the injured portion by intensively irradiating anions to the injured portion and the human body of the

The invention claimed is:

1. An intensive care device using anions comprising:
   a body part in which a main board is mounted in the interior thereof, in which a touchscreen is provided on a front surface thereof, and in which moving wheels are installed on the lower side thereof;
   a head part connected to one side of the body part by an arm hinge to be movable, and in which an anion generating unit electrically connected to the main board is operatively installed;
   an anion irradiating part connected to one side of the head part such that the angle thereof is adjusted and electrically connected to the anion generating unit such that anions generated from the anion generating unit are irradiated to an outside through an end thereof; and a human body grounding device electrically connected to the anion generating unit, and electrically grounded to a portion of the human body of a patient such that the in-air loss of the anions irradiated from the anion irradiating part by an electrostatic induction phenomenon due to grounding of the human body is minimized and the dosage of the anions to the human body of the patient is maximized, wherein the anion irradiating part includes:
  a pair of connecting members connected to the head part in a bellows tube manner such that the angles thereof is adjusted; and
  irradiation members installed at ends of the pair of connecting members, respectively, and configured to irradiate anions, wherein the light irradiation member includes:
  anion irradiating needles protruding from a lower surface of the corresponding one of the pair of irradiation members, the number of which corresponds to the number of the anion generating units, electrically connected to the anion generating unit, and a tip end of which is manufactured in a sharp needle shape such that anions are irradiated through the end thereof;
  a low-output light irradiation lens provided on a lower surface of the corresponding one of the pair of irradiation members to be turned on and off and from which light of a blue wavelength is irradiated; and
  a sensor protruding from a lower surface of the corresponding one of the pair of irradiation members, and extending further than the anion irradiating needle such that an operation of the intensive care device using anions is interrupted when an end of the sensor connected to a portion of the human body, wherein, in a state where the human body of the patient is brought into an electrostatically induced condition due to grounding of the human body by the human body grounding device, when anions are irradiated from the anion irradiating needle to an injured portion of the human body, the anionic charges have straightness and are guided toward the human body of the patient such that the loss of the anions by cations in the air is minimized and the dosage of the anions toward the injured portion is maximized.

2. The intensive care device of claim 1, wherein the anion generating unit includes:

a terminal panel; and
a plurality of anion modules mounted on the terminal panel and configured to generate anions,
wherein the ainon modules are connected to the main board to supply electric power to the main board, are connected to the anion irradiating part to supply anions to the anion irradiating part, and are connected to the human body grounding device such that the human body grounding device is grounded to the human body.

3. The intensive care device of claim 2, wherein each of the anion module includes:
  an oscillation part oscillated and amplified by using a power source voltage to generate an input voltage and providing the generated input voltage to a transformer;
  a transformer configured to boost and output the input voltage;
  a grounding part electrically connecting one end of an output side of the transformer, and an electrode contacting the human body; and
  a high-voltage generating part electrically connected to opposite ends of an output side of the transformer, and configured to convert the boosted voltage of the transformer to a high voltage and provide the high voltage to anion irradiating needles through an output side (HV).

4. The intensive care device of claim 3, wherein the grounding part includes:
  a rectification element, of which one terminal is connected to one end of the output side; and
  a grounding terminal connected to an opposite terminal of the rectification element and the electrode.

5. The intensive care device of claim 3, wherein the high voltage generating part includes: a voltage doubling/rectifying circuit configured to double and rectify voltages of opposite ends of the output side of the transformer.

6. The intensive care device of claim 1, wherein among the plurality of anion modules, a half of the anion modules are electrically connected to one of the anion irradiating needles and a remaining half of the anion modules are electrically connected to another of the anion irradiating needles, and the anion modules electrically connected to the one of the anion irradiating needles and the anion modules electrically connected to the other of the anion irradiating needles are independently electrically connected to the human body grounding device.

* * * * *